US006483926B1

(12) United States Patent
Yamashita et al.

(10) Patent No.: US 6,483,926 B1
(45) Date of Patent: Nov. 19, 2002

(54) FLOOR IMPACT NOISE SUPPRESSOR IN A MULTI-STORIED BUILDING

(75) Inventors: Yasuhiro Yamashita, Nagano (JP); Hiroaki Hiraguri, Komagane (JP)

(73) Assignees: Taisei Electronic Industries Co., Ltd. (JP); Yasihiro Yamashita (JP)

( * ) Notice: Subject to any disclaimer, the term of this patent is extended or adjusted under 35 U.S.C. 154(b) by 943 days.

(21) Appl. No.: 08/688,874

(22) Filed: Jul. 31, 1996

(30) Foreign Application Priority Data

Aug. 3, 1995 (JP) ............................................ 7-216488

(51) Int. Cl.[7] ......................... A61F 11/06; G10K 11/16; H03B 29/00

(52) U.S. Cl. .................... 381/762; 381/71.7; 381/71.14

(58) Field of Search ........................... 381/71, 94, 73.1, 381/71.1, 71.2, 71.3, 71.7, 71.8, 71.9, 71.11, 71.14, FOR 123; 181/206; 52/167.1–167.9

(56) References Cited

U.S. PATENT DOCUMENTS

| | | | |
|---|---|---|---|
| 5,024,288 | A | 6/1991 | Shepherd et al. |
| 5,438,624 | A | 8/1995 | Lewiner et al. |

FOREIGN PATENT DOCUMENTS

| | | | |
|---|---|---|---|
| FR | 94/27283 | | 11/1994 |
| JP | 61-87815 | * | 6/1986 |
| JP | 62-203332 | * | 12/1987 |
| JP | 3-89834 | * | 9/1991 |
| JP | 4-133298 | * | 12/1992 |
| JP | 5-108083 | * | 4/1993 |
| JP | 6-240776 | * | 8/1994 |

* cited by examiner

*Primary Examiner*—Xu Mei
(74) *Attorney, Agent, or Firm*—Rader. Fishman & Grauer PLLC

(57) ABSTRACT

A noise suppressor for reducing propagation of a floor impact noise generated in an upper story to a lower story in a multi-storied building is disclosed. A reference sensor set at a position between a floor of the upper story and a ceiling of the lower story detects a floor impact noise generated in the upper story and converts the noise to an electric signal. This signal is computed and processed by a control unit and transmitted to a speaker located at a position lower than the reference sensor. The speaker emitts a sound wave interfering the floor impact noise to eliminate the noise. The noise not having been suppressed is detected by an error sensor and processed together with the noise detected by the reference sensor by the control unit, thus a sound wave to be emitted from the speaker is corrected appropriately.

13 Claims, 3 Drawing Sheets

FLOOR IMPACT NOISE SUPPRESSOR IN A MULTI-STORIED BUILDING

BACKGROUND OF THE INVENTION

1. Field of the Invention

The present invention relates to a noise suppressor for reducing propagation of a floor impact noise and other types of noise generated in an upper story to a lower story in a two- or more-storied building.

2. Description of the Prior Art

There have been proposed various types of methods as a soundproof means against floor impact noises. For instance, in published Japanese Utility Model Application, KOKAI (Early Publication) No. (hereinafter referred to briefly as "JU-A-") 3-89834, it is taught that arrangement of sound insulating materials each having angular projections formed on the bottom surface thereof on the floor panels makes smaller transmission of vibration to a floor surface and, as a result, a function of noise suppression is enhanced. Also, in JU-A-61-87815 it is taught that the noise suppression effect can be achieved by forming a floor panel body with a foaming material and also forming concave grooves in the rear surface thereof. Furthermore, a floor framing method in which the noise suppression effect can be achieved by incorporating wooden floor joists into the dry-floor construction method is disclosed in JU-A-62-203332.

By the way, apart from the passive noise control obtained by improving material or construction as described above, an active noise control for "eliminating a sound with another type of sound" has been examined and utilized in various fields. For instance, a device which directionally generates an additional sound in a working area against a noise propagated from a noise area on the same floor to locally suppress the noise is disclosed in published Japanese Patent Application, KOKAI No. (hereinafter referred to briefly as "JP-A-") 5-108083. Also, a soundproof device for suppressing mechanical noises made outside a soundproof box with sound waves in the soundproof box installed in a site of a manufacturing line in a factory is disclosed in JP-A-6-240776. In addition to the disclosures described above, JU-A-4-133298 discloses an active system of a noise suppressor for suppressing noises propagating through a duct to rooms also with sound waves in a multiple dwelling house or the like.

These active types of noise control are effective in suppressing noises by basically making use of interference between sound waves therewith although the control systems are more or less different from each other. Namely, the control system described above is based on the principle in which a noise is counteracted by adding a sound wave having a reverse phase and also having the same sound pressure thereto to cause interference between the sound waves to eliminate the noise.

The problem concerning floor impact noises has been increasing in recent years in association with increase of multiple dwelling houses as well as with higher density of environments for living, and especially in constructions based on wooden materials, it has been difficult to take effective countermeasures for reduction of the floor impact noises because there are more components as compared to concrete constructions, or because the construction itself is complicated. In a case where the technology of passive noise control based on improvement of the floor materials or the construction described above is employed, floor impact noises are somewhat reduced, but a sufficient noise suppression effect can not eventually be obtained thereby, and further, there may occur a problem other than those relating to noises that the strength of the floor itself is reduced. Furthermore, an application of the technology of the passive noise control to existing buildings requires an extensive scale of construction works, which is practically difficult to be realized.

There is not any known case in which the technology of active noise control using the interference between sounds has actually been applied to eliminate floor impact noises.

SUMMARY OF THE INVENTION

It is, therefore, an object of the present invention to provide a floor impact noise suppressor which enables floor impact noises and other types of noise (hereinafter referred to collectively as "floor impact noises") to be reduced by applying the technology of active noise control to a two- or more-storied building without changing floor materials or construction and without reducing the strength of the floor itself more effectively as compared to the technology of passive noise control based on the conventional technology.

In accordance with the present invention, to achieve the object described above, there is provided a floor impact noise suppressor for reducing propagation of floor impact noises generated in an upper story to a lower story in a multi-storied building, which comprises a reference sensor for detecting a floor impact noise generated in the upper story and converting it to an electric signal; a sound wave generating means for emitting a sound wave for suppressing the floor impact noise; an error sensor for detecting an interference sound caused by interference between the floor impact noise and the sound wave emitted from the sound wave generating means and converting it to an electric signal; and a controlling means for computing, according to an adaptive control based on the electric signals from the reference sensor and the error sensor, a driving signal for emitting a sound wave adapted to eliminate the floor impact noise by means of negative phase interference from the sound wave generating means, the reference sensor being disposed in the periphery of the floor of the upper story or in any place from the bottom of the floor of the upper story to the bottom surface of the ceiling of the lower story, the sound wave generating means being disposed at a position lower than that of the reference sensor, and the error sensor being disposed inside a room in the lower story.

In a preferred embodiment, it is desirable to use at least two error sensors to more effectively suppress noises by scanning the error sensors one by one and successively updating an impulse response to an adaptive filter, and also it is desirable to use at least two units of sound wave generating means to generate without fail sound waves for eliminating floor impact noises, the sound waves each having a phase reverse to that of the noise to be eliminated. Furthermore, in a multi-storied building, in a case of a heavy weight floor impact noise as defined in JIS (Japanese Industrial Standard) A-1418, generally, the lower the frequency is, the higher a level of the floor impact noise is, and in a case of a light weight floor impact noise, although the level is different according to a floor construction, a peak of the level of the floor impact noise is generally in a range from 25 to 125 Hz (50 to 250 Hz in a model on the scale of one to two (1/2)) in an actual building. It is therefore desirable to set a signal received by the controlling means at a frequency not higher than 200 Hz, preferably not more than 150 Hz in order to effectively suppress a floor impact noise in the low frequency band.

BRIEF DESCRIPTION OF THE DRAWINGS

Other objects, features, and advantages of the invention will become apparent from the following description taken together with the drawings, in which.

DETAILED DESCRIPTION OF THE PREFERRED EMBODIMENTS

The floor impact noise suppressor according to the present invention detects a floor impact noise with a reference sensor and generates a sound wave interfering with the floor impact noise for eliminating the noises by means of a sound wave generating means (hereinafter referred to as a secondary sound source).

Suppression of noises based on these series of effects is called an active control. In the active control, a noise is suppressed by loading a sound wave having a phase reverse to a sound wave to be processed and also having the same amplitude as that of the latter for making use of interference between two sounds to achieve noise suppression. The operating principle is based on the fact that a propagating speed of a sound wave through the air is far slower than that of an electric signal. With this feature, it is possible to compute the detected floor impact noise and to generate a sound wave having reverse phase and the same amplitude within a period of time required for propagation of a floor impact noise from a point where the floor impact noise is detected to a point where the noise is suppressed.

A source of a floor impact noise which is a subject for treatment in the present invention is on the floor in the upper story. To suppress a noise by the active control described above, therefore, it is required to detect the sound wave by the reference sensor, to compute the detected wave, and to generate a sound wave having a phase reverse to and the same amplitude as that of the noise from the secondary sound source by the time when the floor impact noise reaches from the floor in the upper story to a space in which the noise is to be suppressed. Accordingly, it is required that a distance between the secondary sound source and the space to be controlled is shorter than a distance at least between the position of reference sensor and the space to be controlled. Namely, the reference sensor should be positioned as closer to the floor in the upper story as possible, while the secondary sound source should be positioned at a position lower than at least the floor in the upper story.

Further detailed description is made hereinafter for the present invention with reference to embodiments each shown in the attached drawing.

Figure 1:
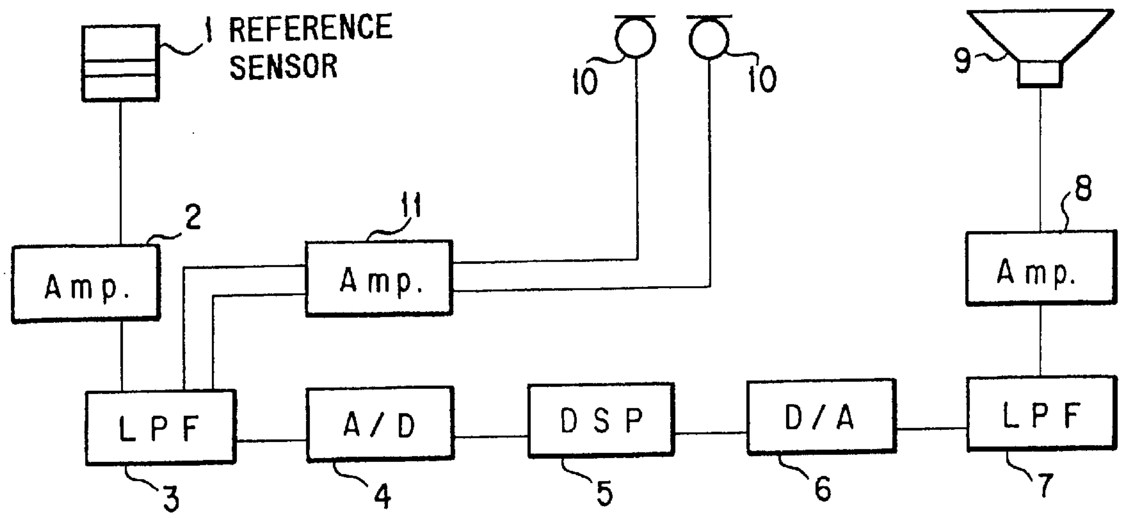
FIG. 1 is a schematic flow diagram of an active control in the floor impact noise suppressor according to the present invention.

FIG. 1 shows a schematic flow diagram of an active control in an embodiment of the floor impact noise suppressor according to the present invention. A floor impact noise is detected and converted to an electric signal by a reference sensor 1 and is amplified by an amplifier (Amp.) 2. Then only a low-frequency signal is taken out by a low-pass filter (LPF) 3, and the signal is converted to a digital signal by an A/D converter 4. The signal is computed and processed by a digital signal processor (DSP) 5 which is the controlling means, wherein a driving signal for emitting a sound wave having a phase reverse to that of the floor impact noise and also having a waveform of the same amplitude as that of the floor impact noise from a speaker 9 as the secondary sound source is generated, and the driving signal is converted to an analog signal by a D/A converter 6. Furthermore, with this signal, a sound wave having a phase reverse to that of the floor impact noise and having the same sound pressure as that of the latter is emitted from the speaker 9 through a low-pass filter (LPF) 7 and an amplifier (Amp.) 8, and this sound wave and the floor impact noise cause phase interference, thus the noise being suppressed. Furthermore, two units of error sensors 10 are incorporated in the floor impact noise suppressor. The error sensor 10 evaluates a rate of suppressing noises, whereby suppression of noises are performed more effectively. Namely, any sound wave not having been suppressed with the interference between the floor impact noise and the sound wave for suppressing the noise is detected by the error sensor 10, is transmitted to the low-pass filter (LPF) 3 through an amplifier (Amp.) 11, and is computed and processed by the digital signal processor (DSP) 5 together with the signal for the floor impact noise detected by the reference sensor 1.

Further detailed description is made for each of the components in the floor impact noise suppressor. First, a microphone or an acceleration pickup may be used as the reference sensor 1. It should preferably be disposed, for instance, in the periphery of the floor in the upper story, or in any place from the bottom of the floor in the upper story to the bottom surface of the ceiling in the lower story.

As the secondary sound source, a speaker, especially a board speaker, is preferable when it is disposed inside a room because of its compact size, and also can advantageously be used in the point that a plane wave can be expected more as compared to the speaker of the conventional type. As for an output of a speaker, if it is too small, a regenerated sound corresponding to an output value from the DSP 5 is not produced, and resultantly the output value from the DSP 5 overflows. Accordingly, it is desirable to use a speaker in which a larger output value can be obtained. There is no specific restriction on the number of speakers to be provided for this purpose, but at least two units thereof are desirable. In a case where a plurality of speakers are used, it is desirable to drive them in the same phase. Also, as a place for the speakers provided, as described above, it is required for a speaker to be positioned lower than the floor in the upper story, but if it is set at a position too low from the ceiling in the lower story, there is an advantage that it can take enough time required for computing a sound wave detected by the reference sensor and a load to the controlling means can slightly be reduced, which in turn makes an area for suppressing noises undesirably smaller. As a place for the speakers provided, anywhere on the ceiling surface of a room in the lower story, or on a wall surface there in is desirable from the view points of practicability and the effect of noise suppression.

Then, a microphone may be used as the error sensor 10. The error sensor is used to detect, as described above, a sound wave which has not been eliminated with the interference between the floor impact noise and the sound wave emitted from the secondary sound source, and any position inside of a room in the lower story is selected as a place for the microphone to be disposed. Although a number of error sensors to be used varies according to the applied system, a 1-1-2 system based on the ES method (error scanning algorithm) can preferably be used as an adaptive algorithm in the present invention, and in this case, a number of error sensors to be provided is two units. "1-1-2" indicates a number of reference sensors, a number of adaptive filters (namely a DSP control system), and a number of error sensors in the order. In this algorithm, signals from the two units of error sensors are alternately computed and processed by the DSP. Namely, an adaptive filtering factor is updated according to an error signal for an instantaneous value provided by one of the error sensors of a certain sampling time, and also the adaptive filtering factor is updated according to that provided by the other error sensor of the next sampling time. In short, error sensors are scanned one by one, and the adaptive filtering factor is updated each time. In a case where this 1-1-2 system is employed, it can be considered, as for places for setting the two units of error sensors, that (a) two units thereof are disposed in midair in the center of a room in the lower story, (b) one is disposed near the ceiling in the center thereof and the other is disposed near the floor in the lower story, or (c) the two units are disposed on wall surfaces opposing each other respectively, but the case (b) is preferable from the view points of practicability and the effect of noise suppression or the like.

As the DSP described above, it is preferable to employ a unit enabling computation at a higher speed. The place for the unit to be installed is not particularly limited, and the unit may integrally be provided with an amplifier, a low-pass filter, an A/D converter, and a D/A converter each of which is another component shown in FIG. 1. The unit may be disposed in the upper story, in the lower story, or in any part of the space between the bottom of the floor in the upper story and the ceiling of the lower story regardless of the places where the reference sensor, secondary sound source, and error sensors are located.

Figure 2:
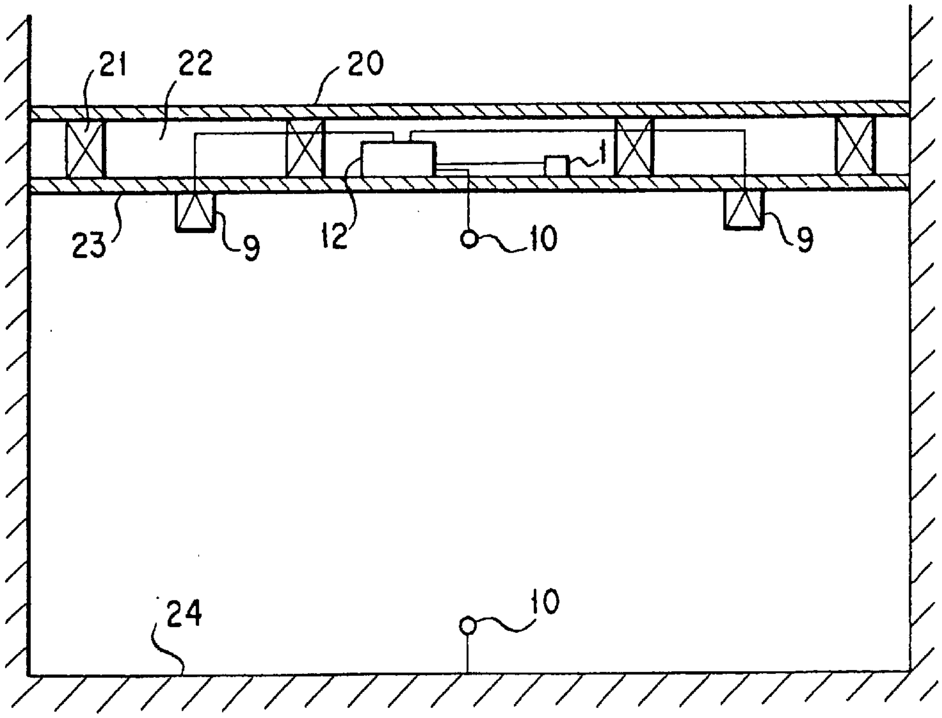
FIG. 2 is a partial longitudinal sectional schematic view showing an embodiment in which the floor impact noise suppressor according to the present invention is provided in a two-storied wooden house.

FIG. 2 shows a partial longitudinal sectional view of a 2-storied wooden house with the floor impact noise suppressor according to the present invention provided therein. In this house, a reference sensor 1 is disposed in a space section 22 between the floor 20 of the second story and the ceiling 23 of the first story to detect a floor impact noise from the floor of the second story. The reference numeral 21 indicates beams. The detected floor impact noise is converted to an electric signal, is transmitted to a control unit 12 disposed in the same space section 22, and is computed by the control unit 12. It should be noted that the control unit 12 incorporates therein the amplifiers (Amp.) 2, 8, 11, low-pass filters (LPF) 3, 7, A/D converter 4, D/A converter 6, and digital signal processor (DSP) 5 each shown in FIG. 1. The computed electric signal is converted to a sound wave for eliminating the floor impact noise, which is emitted from the speaker 9 disposed on the bottom surface of the ceiling 23 of the first story. Furthermore, the sound wave which has not been suppressed is alternatively detected and converted to an electric signal by the two units of error sensor 10 disposed near the ceiling 23 of the first story and on the floor 24 of the first story respectively. The signal is transmitted to the control unit 12 and computed together with the signal from the reference sensor 1 by the control unit 12. The sound wave produced by processing the signals is again emitted from the speaker 9.

As described above, the floor impact noise suppressor according to the present invention actively suppresses a noise by generating a sound interfering and eliminating the floor impact noise. With the floor impact noise suppressor according to the present invention, extensive construction works such as modification of a floor material or construction or the like, conventionally required as means for improving the noise suppression effect, are not required, and the suppressor can easily be provided in wooden houses or the like without any modifications as described above, and also excellent noise suppression effects can be achieved in a multi-storied building regardless of whether the building is a wooden house or a concrete construction or the like. Furthermore, most of the components of the present apparatus can be accommodated in a space between a ceiling of the lower story and a floor of the upper story, which does not make the space for living narrower.

Experiment 1

It was examined how a noise suppression effect would be affected by location of the reference sensors.

A house to be examined was a 2-storied house built according to the constructing method based on the conventional technology, and both of the upper vibration-created room and the lower sound-receiving room were 8-mat rooms. A processing for sound absorption had not been executed in the sound-receiving room. The floor in the second story was constructed from beams, joists, and laminated floor panels each comprising a plywood for construction (a thickness of 12 mm), cushion rubber (a thickness of 8 mm), ALC floor material (a thickness of 37 mm), and plywood for construction (a thickness of 12 mm).

Figure 3:
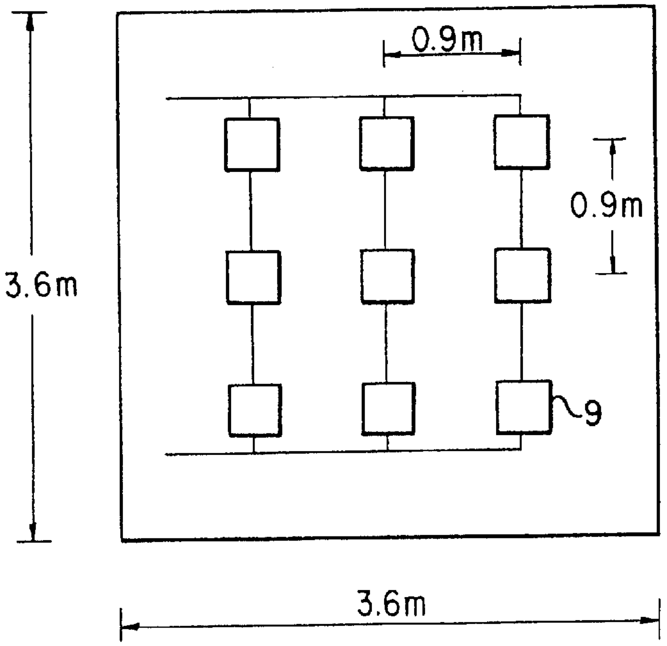
FIG. 3 is a plan view showing positions where speakers are disposed in experiments 1 and 2.
Figure 4:
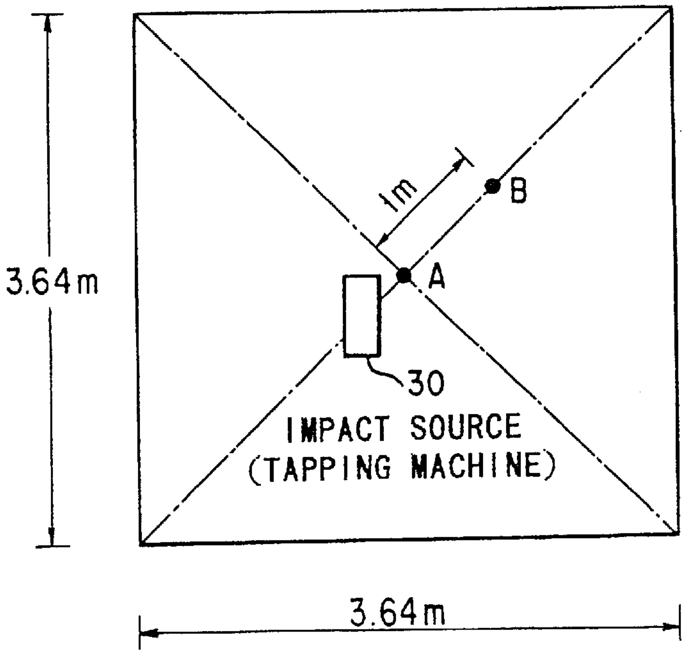
FIG. 4 is a plan view showing positions where reference sensors (acceleration pickups) are disposed in experiments 1 and 2.

A schematic flow of the active control system was the same as that shown in FIG. 1, and parameters for the active control were set as follows; a sampling frequency: 1500 Hz, a unified tap length: 256, a tap length of an adaptive filter: 512, and a cut-off frequency of a low-pass filter: 100 Hz. As a secondary sound source, to obtain a required output, totally nine units of small speaker 9 (Audio-Technica AT-SP39AV) were provided at dispersed positions spaced from each other with an equal space (900 mm) in the ceiling as shown in FIG. 3, and they were driven in the same phase. A microphone was used as an error sensor 10. An acceleration pickup was used as a reference sensor 1, and as shown in FIG. 4, it was disposed in the center of the floor in the second story (a point A) or at a position one meter away from the center thereof (a point B).

A light weight floor impact source 30 (a tapping machine) was placed in the central part of the floor of the second story for generating a floor impact noise to be processed, and to eliminate the variation in noises for each tapping, the noise was generated by using one piece of weight (by tapping twice a second). It should be noted that the result of each experiment shows an arithmetic mean of 32 values obtained at the position of each error sensor.

Figure 5:
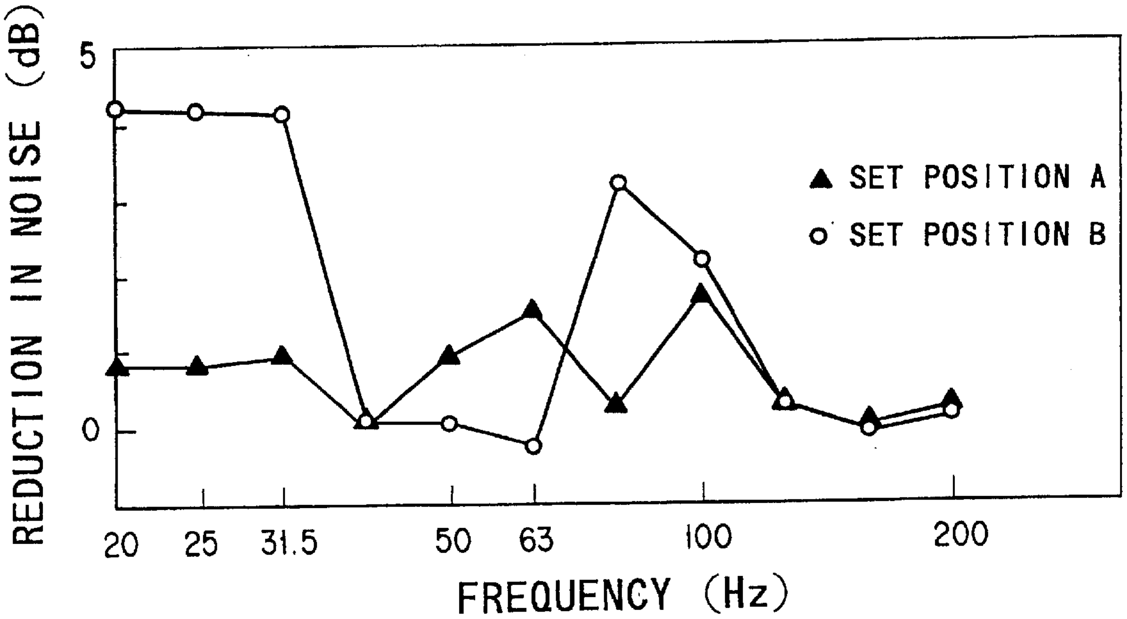
FIG. 5 is a graph showing how the effect of suppressing noises is affected by a position where the reference sensor is disposed.

FIG. 5 shows the results of the experiment. As clearly shown by the figure, although a sound to be processed has a peak in a low-pitched sound range (in a band of 25 Hz) for the control points, the effect does not appear therein in a case where a pickup is set at a point A. The reason is presumably that a floor impact noise property received by the pickup varies in the low-pitched sound range according to a position where the pickup is placed. In a case where the pickup is set at the point A, in contrast to a case where the pickup is set at a point B, it is recognized that a signal in the low-pitched sound range (in a band from 25 to 31.5 Hz) can hardly be extracted. It is considered to be difficult for the pickup to extract the property of the low-pitched sound range unless the floor impact noise propagates through a certain distance. From the experiment described above, if it is disposed on a floor of the upper story, a reference sensor should preferably be disposed in the periphery thereof and the central part thereof having a large flection should be avoided as much as possible. More preferably, the disposition of the reference sensor in a space between the floor of the upper story and the ceiling of the lower story will be practical.

Experiment 2

Figure 6:
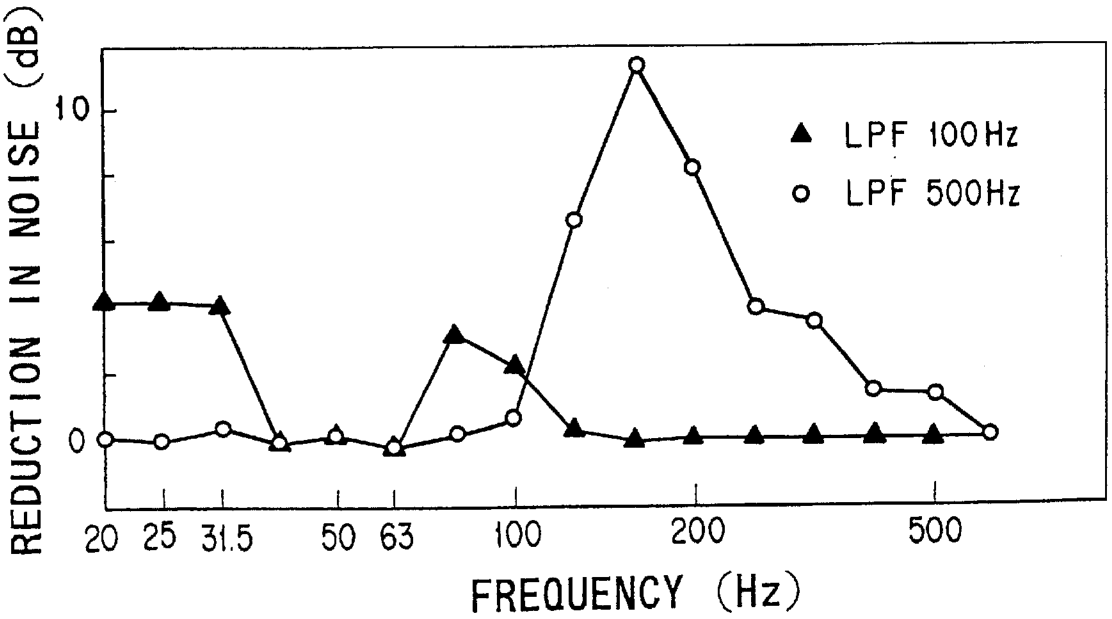
FIG. 6 is a graph showing how the effect of suppressing noises is affected by a cut-off frequency of a low-pass filter.

It was examined how a noise suppression effect would be affected by a cut-off frequency of a low-pass filter. Namely, the experiment was carried out under the same conditions as those in the experiment 1 excluding the fact that a cut-off frequency was set to 100 Hz or to 500 Hz. FIG. 6 shows the results of the experiment.

As clearly understood from the figure, when signals up to a high band are processed with a high cut-off frequency, no effect is obtained in the low-pitched sound range which includes a peak of the floor impact noise. Although the effect varies according to the floor construction, generally the light weight floor impact noise has its peak in a band from 25 Hz to 125 Hz as described above. Accordingly, it is desirable to set a cut-off frequency of a low-pass filter in this band so as to effectively suppress floor impact noises, and generally the cut-off frequency should be not more than 200 Hz, preferably not more than 150 Hz. However, in the active control of a heavy weight floor impact noise, there is not a large difference in the noise suppression effect even if a cut-off frequency is changed.

While certain specific embodiments have been disclosed herein, the invention may be embodied in other specific forms without departing from the spirit or essential characteristics thereof. The described embodiments are therefore to be considered in all respects as illustrative and not restrictive, the scope of the invention being indicated by the appended claims rather than by the foregoing description and all changes which come within the meaning and range of equivalency of the claim are, threrefore, intended to be embraced therein.

What is claimed is:

1. A floor impact noise suppressor for reducing propagation of floor impact noises having a sound wave frequency of not more than about 500 Hz, generated in an upper story to a lower story in a multi-storied building, comprising:

a reference sensor for detecting a floor impact noise generated in the upper story and converting it to an electric signal;

a speaker for emitting a sound wave for suppressing the floor impact noise;

an error sensor for detecting an interference sound caused by interference between the floor impact noise and the sound wave emitted from said speaker and converting it to an electric signal; and a controlling means for computing, according to an adaptive control based on the electric signals each from said reference sensor and error sensor, a driving signal for emitting a sound wave adapted to eliminate the floor impact noise by means of negative phase interference from said speaker, said reference sensor being disposed in a periphery of a floor of the upper story or in any place from a bottom of the floor of the upper story to a bottom surface of a ceiling of the lower story;

said speaker being disposed at a position lower than that where said reference sensor is disposed; and said error sensor being disposed. inside a room in the lower story.

2. The floor impact noise suppressor according to claim 1, which comprises at least two error sensors.

3. The floor impact noise suppressor according to claim 1, which comprises at least two speakers.

4. The floor impact noise suppressor according to claim 1, wherein a signal received by said controlling means is a signal having a low frequency of not more than 200 Hz.

5. The floor impact noise suppressor according to claim 1, wherein said reference sensor is a microphone or an acceleration pickup.

6. The floor impact noise suppressor according to claim 1, wherein said speaker is a board speaker.

7. The floor impact noise suppressor according to claim 1, wherein said error sensor is a microphone.

8. A floor impact noise suppressor for reducing propagation of floor impact noises, having a sound wave frequency of not more than about 500 Hz, generated in an upper story to a lower story in a multi-storied building, comprising:

a reference sensor for detecting a floor impact noise generated in the upper story and converting it to an electric signal, said reference sensor being disposed in a periphery of a floor of the upper story or in any place from a bottom of the floor of the upper story to a bottom surface of a ceiling of the lower story;

a speaker for emitting a sound wave for suppressing the floor impact noise, said speaker being disposed at a position lower than that where said reference sensor is disposed;

an error sensor for detecting an interference sound caused by interference between the floor impact noise and the sound wave emitted from said speaker and converting it to an electric signal, said error sensor being disposed inside a room in the lower story;

means for converting any signal having a low frequency of not more than 200 Hz among the electric signals each transmitted from said reference sensor and error sensor to a digital signal and transmitting it to a controlling means;

a controlling means for computing, according to an adaptive control based on the signal transmitted from said converting means, a driving signal for emitting a sound wave having a phase reverse to that of said floor impact noise and also having a waveform with the same amplitude as that of said impact noise from said speaker; and means for converting said driving signal to an analog signal and transmitting it to said speaker.

9. The floor impact noise suppressor according to claim 2, wherein said error sensors are disposed near the ceiling and near a floor of the lower story.

10. The floor impact noise suppressor according to claim 2, wherein said error sensors are disposed on wall surfaces of the room in the lower story.

11. The floor impact noise suppressor according to claim 8, wherein said reference sensor is a microphone or an acceleration pickup.

12. The floor impact noise suppressor according to claim 8, wherein said error sensor is microphone.

13. The floor impact noise suppressor according to claim 8, which comprises at least two error sensors, the error sensors being disposed near the ceiling and near a floor of the lower story.

* * * * *

UNITED STATES PATENT AND TRADEMARK OFFICE
CERTIFICATE OF CORRECTION

PATENT NO. : 6,483,926 B1 
DATED : November 19, 2002
INVENTOR(S) : Yasuhiro Yamashita et al.

It is certified that error appears in the above-identified patent and that said Letters Patent is hereby corrected as shown below:

Column 8,
Line 61, "is microphone." should read -- is a microphone --.

Signed and Sealed this

Twenty-ninth Day of April, 2003

JAMES E. ROGAN
*Director of the United States Patent and Trademark Office*